US006592583B2

United States Patent
Hirano et al.

(10) Patent No.: US 6,592,583 B2
(45) Date of Patent: Jul. 15, 2003

(54) PERFUSATE SUPPLY APPARATUS FOR ELECTRIC BIPOLAR TWEEZERS AND SURGICAL PROCEDURE WITH ELECTRIC BIPOLAR TWEEZERS

(75) Inventors: Shinichi Hirano, c/o Kabushiki Kaisha Tokai Rika Denki Seisakusho, 260, Toyota 3-chome, Ohguchi-cho, Niwa-gun, Aichi 480-0195 (JP); Masato Shibuya, 5988-2, Okusa, Komaki-shi, Aichi 485-0802 (JP)

(73) Assignees: Shinichi Hirano, Aichi (JP); Masato Shibuya, Aichi (JP)

( * ) Notice: Subject to any disclaimer, the term of this patent is extended or adjusted under 35 U.S.C. 154(b) by 149 days.

(21) Appl. No.: 09/796,574

(22) Filed: Feb. 27, 2001

(65) Prior Publication Data

US 2001/0051805 A1 Dec. 13, 2001

(51) Int. Cl.[7] .......................... A61B 18/12; A61B 17/30
(52) U.S. Cl. .............................. 606/52; 606/50
(58) Field of Search .............................. 606/50, 51, 52, 606/32, 37–49; 607/96–99

(56) References Cited

U.S. PATENT DOCUMENTS

| 4,567,890 A | 2/1986 | Ohta et al. ............. 128/303.13 |
| 5,464,405 A | 11/1995 | Fujitsu et al. ................ 606/51 |
| 5,554,172 A | * 9/1996 | Horner et al. ................ 607/88 |
| 6,048,341 A | 4/2000 | Hirakawa et al. ............. 606/51 |
| 6,210,411 B1 | * 4/2001 | Hofmann et al. ............. 606/52 |
| 6,228,084 B1 | * 5/2001 | Kirwan, Jr. .................. 606/52 |

FOREIGN PATENT DOCUMENTS

| JP | 11-47152 | * 2/1999 |
| JP | 2000-201947 | 7/2000 |
| JP | 2000-201948 | 7/2000 |

OTHER PUBLICATIONS

Research Discl. 410019, Jun. 1998.*

* cited by examiner

Primary Examiner—John A. Jeffery
(74) Attorney, Agent, or Firm—Jenkens & Gilchrist, P.C.

(57) ABSTRACT

Electric bipolar tweezers include a pair of elongated portions that extend from a base of the tweezers in a forked manner. An electrode is located on the distal end of each electrode. When a legion is held between the elongated portions, high-frequency current is supplied to the electrodes. A perfusate tube is attached to the tweezers and has an outlet that opens near one electrode. A gas line is connected to an intermediate portion of the perfusate tube. Gas is thus mixed with perfusate in the perfusate tube such that perfusate mist is blown from the outlet of the perfusate tube. The mist blows away perfusate between the electrodes, thus preventing the electrodes from short-circuiting.

17 Claims, 4 Drawing Sheets

PERFUSATE SUPPLY APPARATUS FOR ELECTRIC BIPOLAR TWEEZERS AND SURGICAL PROCEDURE WITH ELECTRIC BIPOLAR TWEEZERS

BACKGROUND OF THE INVENTION

The present invention relates to apparatuses for supplying perfusate to electric bipolar tweezers used for hemostasis or incision, which are performed mainly in neurosurgeries, and surgical procedures with these tweezers.

Generally, electric bipolar tweezers are used in neurosurgeries. A typical pair of electric bipolar tweezers include a pair of elongated portions, which extend from a base of the tweezers in a forked manner. An electrode is secured to a distal end of each elongated portion. The electrodes thus oppose each other. A high-frequency wave generating device is connected to the base of the tweezers through a cable. The device supplies high-frequency current to the electrodes. The tweezers are coated with insulating material except for the electrodes. When a lesion of tissue or blood vessel is held between the distal ends of the elongated portions, high-frequency current is supplied to the electrodes. This coagulates blood in the legion due to an effect in accordance with so-called Joule's law, thus accomplishing hemostasis. The legion is cut through electric discharge when necessary.

During the procedure, the legion is heated by the high-frequency current and affects healthy tissue around the legion. To avoid this, a perfusion tube for cooling the legion extends along an inner side of one elongated portion. The tube is connected to a perfusate container, which contains saline, and has an outlet that opens near the electrode of the associated elongated portion. Saline is supplied to the legion from the outlet of the perfusate tube when performing hemostasis or incision on the legion with the tweezers. This cools the legion and healthy tissue around the legion.

When the tweezers hold the legion, the electrodes are located relatively close to each other. In this state, saline may be retained between the electrodes, thus short-circuiting the electrodes. This may hamper hemostasis or incision performed with the tweezers.

SUMMARY OF THE INVENTION

Accordingly, it is an objective of the present invention to provide a perfusate supply apparatus and a surgical procedure that prevent perfusate from being retained between a pair of electrodes of electric bipolar tweezers.

To achieve the foregoing and other objectives and in accordance with the purpose of the present invention, the invention provides a perfusate supply apparatus for electric bipolar tweezers. The tweezers include a pair of elongated portions that extend from a base of the tweezers in a forked manner, and an electrode is located on a distal end of each elongated portion. The apparatus comprises a perfusate tube, wherein a perfusate flows in the perfusate tube, and the perfusate tube is attached to the tweezers and has an outlet that opens near one electrode, a perfusate pump, which sends the perfusate to the perfusate tube, and a gas line, wherein a gas flows in the gas line, and the gas line is connected to an intermediate portion of the perfusate tube for mixing the gas with the perfusate such that a perfusate mist is blown from the outlet of the perfusate tube.

The present invention also provides a perfusate supply apparatus for electric bipolar tweezers. The tweezers include a pair of elongated portions that extend from a base of the tweezers in a forked manner, and an electrode is located on a distal end of each elongated portion. The apparatus comprises a perfusate tube, wherein a perfusate flows in the perfusate tube, and the perfusate tube is attached to the tweezers and has a perfusate outlet that opens near one electrode, a perfusate pump, which sends the perfusate to the perfusate tube to be discharged from the perfusate outlet, and a gas line, wherein a gas flows in the gas line, the gas line is attached to the tweezers and has a gas outlet that opens toward the electrodes, and the gas discharged from the gas outlet blows away the perfusate between the electrodes.

The present invention further provides a surgical procedure with electric bipolar tweezers. The tweezers include a pair of elongated portions that extend from a base of the tweezers in a forked manner, and an electrode is located on a distal end of each elongated portion. The procedure comprises a step of supplying a high-frequency current to the electrodes while a legion is held between the distal ends of the elongated portions for performing hemostasis or incision on the legion, and a step of blowing a perfusate mist toward the electrodes from an outlet of a perfusate tube attached to the tweezers for cooling the legion and the vicinity of the legion, wherein the perfusate mist blows away the perfusate between the electrodes.

The present invention further provides a surgical procedure with electric bipolar tweezers. The tweezers include a pair of elongated portions that extend from a base of the tweezers in a forked manner, and an electrode is located on a distal end of each elongated portion. The procedure comprises a step of supplying a high-frequency current to the electrodes while a legion is held between the distal ends of the elongated portions for performing hemostasis or incision on the legion, a step of discharging a perfusate toward the electrodes from an outlet of a perfusate tube attached to the tweezers for cooling the legion and the vicinity of the legion, and a step of blowing a gas toward the electrodes from a gas outlet of a gas line attached to the tweezers for blowing away the perfusate between the electrodes.

Other aspects and advantages of the invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings.

DETAILED DESCRIPTION OF THE PREFERRED EMBODIMENTS

First Embodiment

Figure 1:
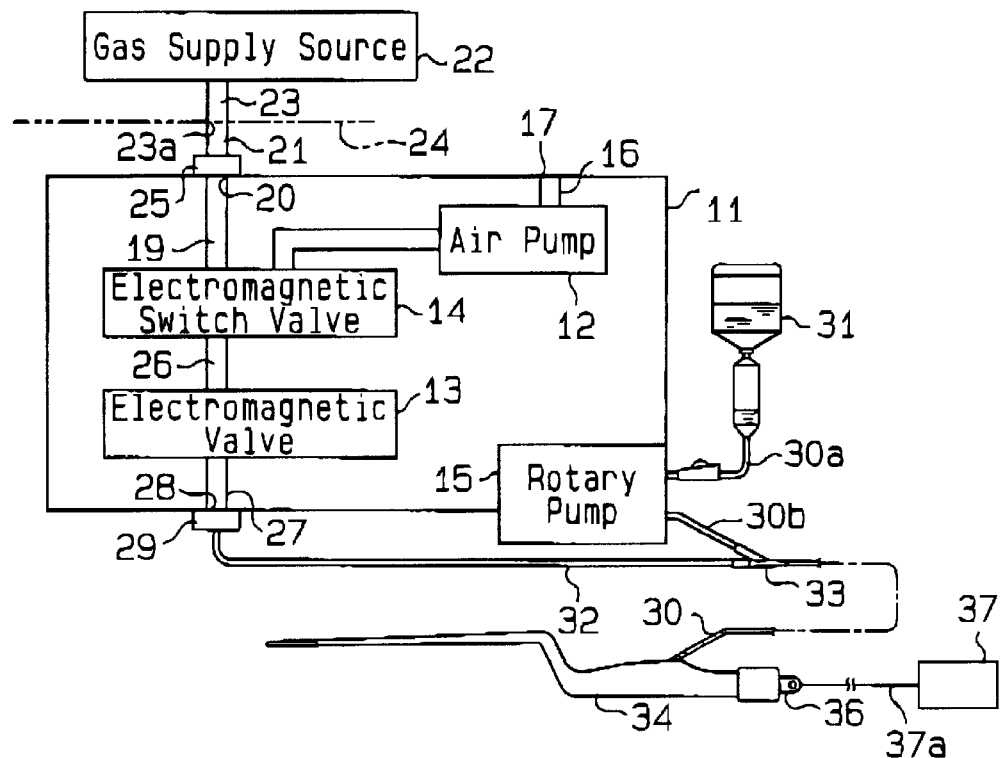
FIG. 1 is a schematic diagram showing electric bipolar tweezers and a perfusate supply apparatus of a first embodiment according to the present invention.

A first embodiment of the present invention will now be described with reference to FIGS. 1 to 3. As shown in FIG. 1, a perfusate supply apparatus includes a control box 11 provided in an operating room. The control box 11 accommodates an air pump 12, an electromagnetic valve 13, an electromagnetic switch valve 14, and a rotary pump 15.

A first inlet pipe 16 is connected to the inlet of the air pump 12. The first inlet tube 16 includes an inlet 17. The inlet 17 has an opening formed in an outer side of the control box 11. The air pump 12 sends ambient air from the exterior of the control box 11, or the operating room, to the interior of the control box 11. The outlet of the air pump 12 is connected to a first inlet port of the electromagnetic switch valve 14 through a first connecting pipe 18. A second connecting pipe 1 is connected to a second inlet port of the electromagnetic switch valve 14. The second connecting pipe 19 has an inlet 20 that opens to the exterior of the control box 11. The control box 11 has a connector 25 at a position corresponding to the inlet 20.

A gas supply source 22 is installed at a predetermined location in a medical institute. The gas supply source 22 includes a gas supply pipe 23 that extends through a wall 24 of the operating room. The supply pipe 23 has a supply port 23a that opens to the interior of the operating room. The supply port 23a is connected to a second inlet pipe 21. The second inlet pipe 21 is detachably attached to the control box 11 through the connector 25, thus connecting the second inlet pipe 21 to the inlet 20. The second connecting pipe 21 has a manually operated valve (not shown). The gas supply source 22 sends compressed carbon dioxide gas, which is incombustible, to the supply pipe 23.

The outlet port of the electromagnetic switch valve 14 is connected to the inlet port of the electromagnetic valve 13 through a third connecting pipe 26. The switch valve 14 is a three-position type and has a valve body that is switched among three positions. The positions include a disconnecting position, a first connecting position, and a second connecting position. If the valve body is located at the disconnecting position, the first and second connecting pipes 18, 19 are disconnected from the third connecting pipe 26. If the valve body is located at the first connecting position, the first connecting pipe 18 is connected to the third connecting pipe 26. If the valve body is located at the second connecting position, the second connecting pipe 19 is connected to the third connecting pipe 26.

A fourth connecting pipe 27 is connected to the outlet port of the electromagnetic valve 13. The fourth connecting pipe 27 is connected to an outlet hole 28 formed in the wall of the control box 11. A bactericidal filter 29 is detachably attached to an outer side of the wall of the control box 11 at a position corresponding to the hole 28. A used filter 29 is removed from the wall for cleaning or is replaced with a new filter 29.

A perfusate tube 30 has an inlet line 30a and an outlet line 30b. The inlet line 30a extends from the inlet of the rotary pump 15, and the outlet line 30b extends from the outlet of the rotary pump 15. The inlet line 30a is connected to a container 31. The container 31 contains perfusate, which is saline in this embodiment.

The upstream end of a gas line 32 is connected to the hole 28 through the filter 29. The downstream end of the gas line 32 is connected to an intermediate portion of the outlet line 30b through a Y-shaped tube 33. The downstream end of the outlet line 30b is connected to a pair of electric bipolar tweezers 34. The section of the perfusate tube 30 downstream of the Y-shaped tube 33 also functions as a gas passage.

Figure 2:
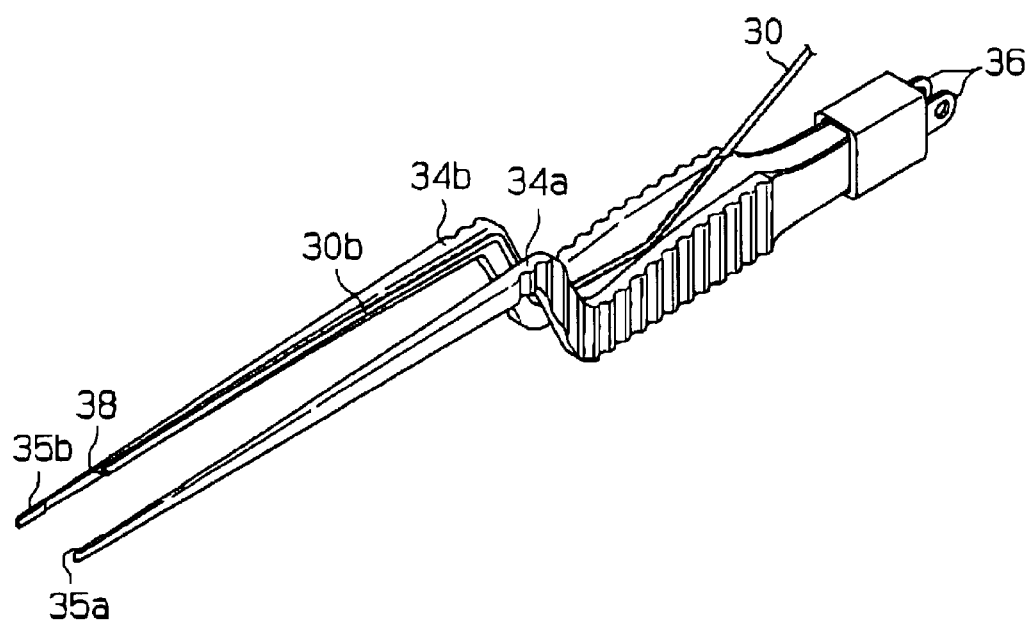
FIG. 2 is a perspective view showing the tweezers of FIG. 1.

As shown in FIG. 2, the tweezers 34 include a pair of elongated portions 34a, 34b, which extend from a base of the tweezers 34 in a forked manner. An electrode 35a is secured to the distal end of the elongated portion 34a, and an electrode 35b is secured to the distal end of the elongated portion 34b. The electrodes 35a, 35b oppose each other. A connector 36 is provided at the base of the tweezers 34. The connector 36 is connected to a high-frequency wave generating device 37 through a cable 37a. The high-frequency wave generating device 37 supplies high-frequency current to the electrodes 35a, 35b. The tweezers 34 are coated with insulating material except for the electrodes 35a, 35b.

The outlet line 30b extends along an inner side of the elongated portion 34b. The outlet line 30b has an outlet 38 that opens near the electrode 35b of the elongated portion 34b. The outlet 38 is spaced from the electrode 35b toward the proximal end of the elongated portion 34b and faces the electrode 35b. The outlet 38 functions as a perfusate supply port and a gas blower.

The electric configuration of the perfusate supply apparatus will hereafter be described.

Figure 3:
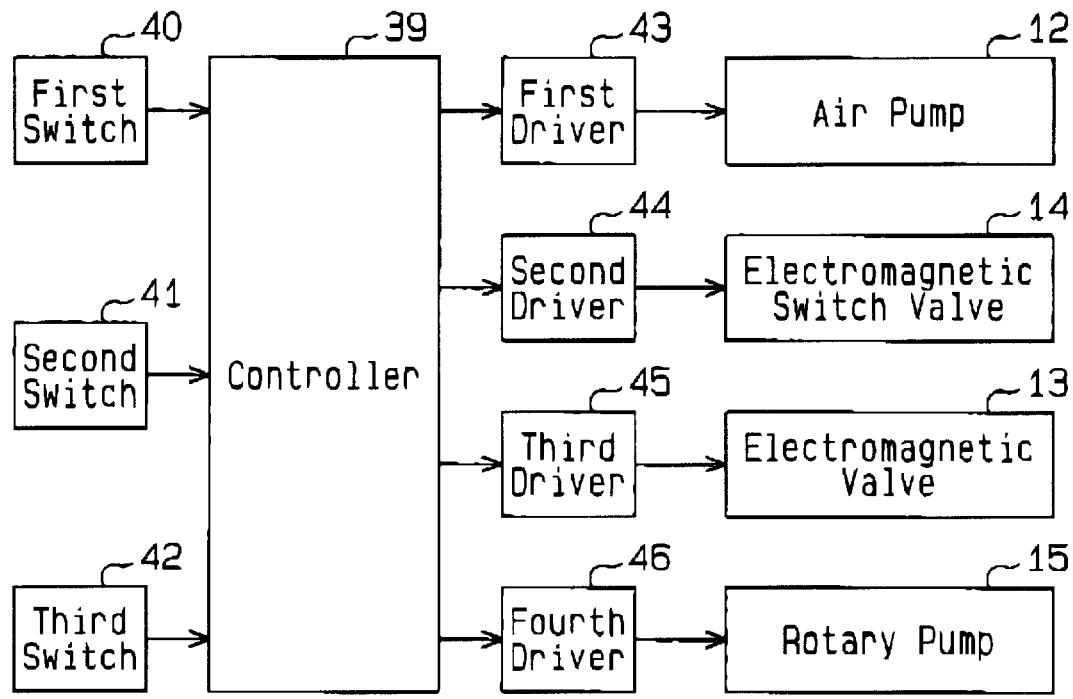
FIG. 3 is a block diagram showing a circuit formed by the perfusate supply apparatus of FIG. 1.

As shown in FIG. 3, a first switch 40, a second switch 41, and a third switch 42 are connected to a controller 39, which is, for example, a computer. The first switch 40 is selectively turned on and off for activating or de-activating the air pump 12. The second switch 41 is selectively switched among a turned-off state, a first turned-on state, and a second turned-on state. In this manner, the electromagnetic switch valve 14 is switched among the disconnecting position, the first connecting position, and the second connecting position. The third switch 42 is selectively turned on and off for activating or de-activating the electromagnetic valve 13 and the rotary pump 15 at the same time. The controller 39 controls the air pump 12, the electromagnetic switch valve 14, the electromagnetic valve 13, and the rotary pump 15 through a first driver 43, a second driver 44, a third driver 45, and a fourth driver 46, respectively.

Although not illustrated in FIG. 1, the first to third switches 40 to 42 are located on an outer side of the wall of the control box 11 such that an operator can manually operate the switches 40 to 42. The controller 39 and the first to fourth drivers 43 to 46 are accommodated in the control box 11.

If the first switch 40 is turned off, the air pump 12 is de-activated. If the first switch 40 is turned on, the controller 39 activates the air pump 12 through the first driver 43.

If the second switch 41 is turned off, the electromagnetic switch valve 14 is switched to the disconnecting position. The first and second connecting pipes 18, 19 are thus disconnected from the third connecting pipe 26. If the second switch 41 is switched to the first turned-on state, the controller 39 operates to switch the electromagnetic switch valve 14 to the first connecting position through the second driver 44. In this state, the first connecting pipe 18 is connected to the third connecting pipe 26. If the second switch 41 is switched to the second turned-on state, the controller 39 operates to switch the electromagnetic switch valve 14 to the second connecting position through the second driver 44. This connects the second connecting pipe 19 to the third connecting pipe 26.

If the third switch 42 is turned off, the electromagnetic valve 13 is closed while the rotary pump 15 is de-activated.

If the third switch 42 is turned on, the controller 39 opens the electromagnetic valve 13 through the third driver 45 and activates the rotary pump 15 through the fourth driver 46 at the same time.

The operation of the tweezers 34 will now be described.

When air is used as compressed gas, the second switch 41 is switched to the first turned-on state. In this state, the electromagnetic switch valve 14 connects the first connecting pipe 18 to the third connecting pipe 26.

Subsequently, the first switch 40 is turned on. The air pump 12 thus draws air from the exterior of the control box 11 through the inlet 17 and compresses the air. The air is then sent to the third connecting pipe 26 through the first connecting pipe 18 and the electromagnetic switch valve 14.

After or when the first switch 40 is turned on, the third switch 42 is also turned on. This opens the electromagnetic valve 13 while activating the rotary pump 15. In this state, compressed air is sent from the third connecting pipe 26 to the gas line 32 through the electromagnetic valve 13 and the fourth connecting pipe 27. The filter 29, which is located between the fourth connecting pipe 27 and the gas line 32, removes foreign objects from the compressed air and sends only clean air to the gas line 32.

The rotary pump 15 sends saline from the container 31 to the tweezers 34 through the perfusate tube 30. Meanwhile, compressed air is sent from the gas line 32 to the perfusate tube 30 through the Y-shaped tube 33 and is mixed with saline in the perfusate tube 30. The mixture of saline and compressed air is then discharged from the outlet 38 of the perfusate tube 30. In other words, saline mist is blown from the outlet 38.

Next, a surgical procedure on a legion of tissue or blood vessel with the tweezers 34 is initiated. More specifically, the legion is first held between the distal ends of the elongated portions 34a, 34b. In this state, the high-frequency wave generating device 37 supplies high-frequency current to the electrodes 35a, 35b. Hemostasis is thus performed on the legion due to an effect in accordance with so-called Joule's law, and the legion is cut through electric discharge when necessary.

Although the high-frequency current heats the legion during the procedure with the tweezers 34, the legion and healthy tissue around the legion are cooled by saline mist, which is blown from the outlet 38 toward the electrodes 35a, 35b. This prevents the heated legion from affecting the healthy tissue. Supply of saline mist is adjusted to cool the legion and healthy tissue around the legion without hampering the procedure with the tweezers 34.

When the tweezers 34 hold the legion, the electrodes 35a, 35b are located relatively close to each other. However, since saline supplied from the outlet 38 to the legion and the healthy tissue is mist, the saline is not retained between the electrodes 35a, 35b. This prevents saline from short-circuiting the electrodes 35a, 35b such that the procedure with the tweezers 34 is reliably accomplished. Further, saline mist blown from the outlet 38 washes blood away from the legion. The legion is thus clearly visible.

If carbon dioxide gas is used instead of compressed air, the second switch 41 is first switched to the second turned-on state. The electromagnetic switch valve 14 thus connects the second connecting pipe 19 to the third connecting pipe 26. Subsequently, the manually operated valve (not shown) in the second inlet pipe 21 is opened. In this state, the gas supply source 22 sends carbon dioxide to the third connecting pipe 26 through the supply pipe 23, the second inlet pipe 21, the second connecting pipe 19, and the electromagnetic switch valve 14.

After or when the manually operated valve is opened, the third switch 42 is turned on. This opens the electromagnetic valve 13 while activating the rotary pump 15. Compressed carbon dioxide gas is thus sent from the third connecting pipe 26 to the gas line 32 through the electromagnetic valve 13 and the fourth connecting pipe 27. Meanwhile, saline is sent from the container 31 to the tweezers 34 through the perfusate pipe 30. Thus, like the case in which compressed air is used, saline most is blown from the outlet 38 of the perfusate tube 30.

Since carbon dioxide gas is incombustible, a spark from the electrode 35a, 35b, if any, does not burn the gas.

The first embodiment has the following advantages.

Since saline supplied to the legion and healthy tissue around the legion is mist, the saline is not retained between the electrodes 35a, 35b. This prevents saline from short-circuiting the electrodes 35a, 35b, thus improving performance of the tweezers 34. In other words, it is unnecessary to increase high-frequency current for maintaining the performance of the tweezers 34, which is otherwise lowered by short-circuit of the electrodes 35a, 35b. Accordingly, the surgical procedure is performed optimally with relatively small high-frequency current.

The saline mist blown from the outlet 38 washes blood away from the legion. The legion is thus clearly visible.

The third switch 24 of the control box 11 is manually operated to selectively open and close the electromagnetic valve 13. That is, the supply of carbon dioxide gas from the gas supply source 22 is easily started or stopped. The gas supply can be stopped when the gas in not in use, thus saving the gas.

The gas sent to the gas line 32, which is ambient air or carbon dioxide gas, is easily selected by manually operating the second switch 41 of the control box 11.

The gas supply source 22, which supplies carbon dioxide gas, is provided separately from the control box 11. The control box 11 is thus relatively small.

If the third switch 42 is turned on, the electromagnetic valve 13 is opened while the rotary pump 15 is activated. In other words, saline and gas start to flow into the perfusate tube 30 at the same time. Thus, immediately after the third switch 42 is turned on, saline mist is blown from the outlet 38. This prevents saline or gas from being blown alone from the outlet 38 before forming a mixture with the other.

Second Embodiment

Figure 4:
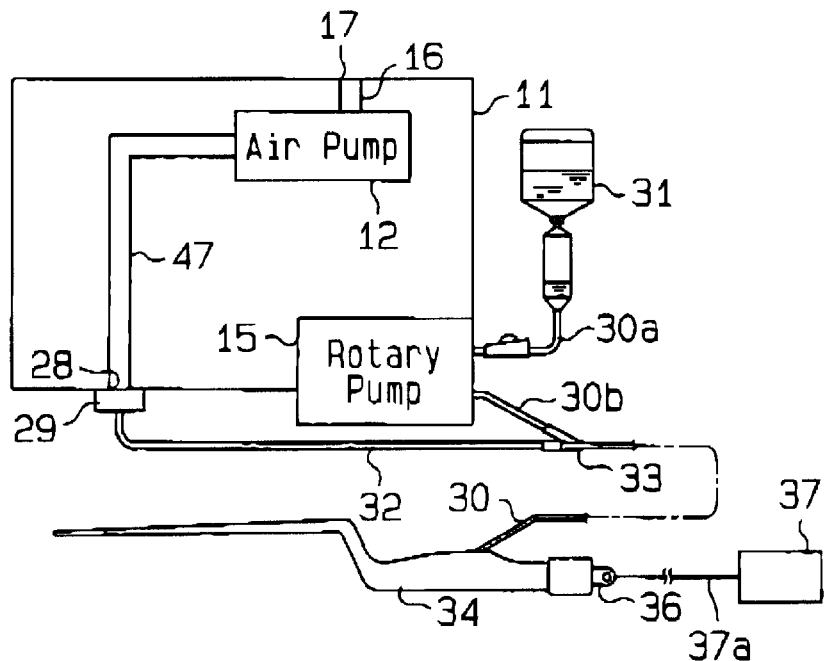
FIG. 4 is a schematic diagram showing electric bipolar tweezers and a perfusate supply apparatus of a second embodiment according to the present invention.

A second embodiment of the present invention will hereafter be described with reference to FIGS. 4 and 5. The description focuses on a difference between the second embodiment and the first embodiment, which is illustrated in FIGS. 1 to 3. More specifically, as shown in FIG. 4, the second embodiment does not include the electromagnetic valve 13 or the electromagnetic switch valve 14 or the gas supply source 22, which are illustrated in FIG. 1. The outlet of the air pump 12 is connected to the hole 28 through a connecting pipe 47.

Figure 5:
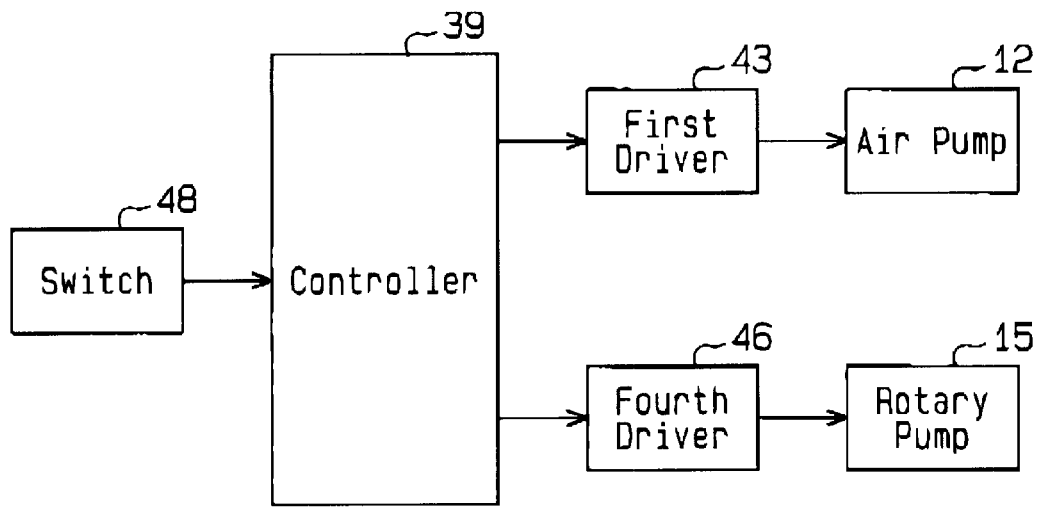
FIG. 5 is a block diagram showing a circuit formed by the perfusate supply apparatus of FIG. 4.

As shown in FIG. 5, a single switch 48 is connected to the input of the controller 39. The switch 48 is selectively turned on and off to activate or de-activate the air pump 12 and the rotary pump 15 at the same time. The switch 48 is located on an outer side of the wall of the control box 11.

The operation of the perfusate supply apparatus of the second embodiment will hereafter be described.

First, the switch 48 is turned on to activate the air pump 12 and the rotary pump 15 at the same time. The air pump 12 draws air from the exterior of the control box 11 through the inlet 17. The air is sent to the perfusate tube 30 through the connecting pipe 47, the filter 29, and the gas line 32.

Meanwhile, the rotary pump 15 sends saline from the container 31 to the tweezers 34 through the perfusate tube 30. Accordingly, like the first embodiment illustrated in FIGS. 1 to 3, saline mist is blown from the outlet 38 of the perfusate tube 30.

The second embodiment is configured relatively simple as compared to the first embodiment. The control box 11 is thus relatively small, and the perfusate supply apparatus is manufactured with low cost. Further, when the switch 48 is turned on, saline and air start to flow into the perfusate tube 30 at the same time. In other words, immediately after the switch 48 is turned on, saline mist is blown from the outlet 38 of the perfusate tube 30. This prevents saline or air from being blown alone from the outlet 38 before forming a mixture with the other.

Third Embodiment

Figure 6:
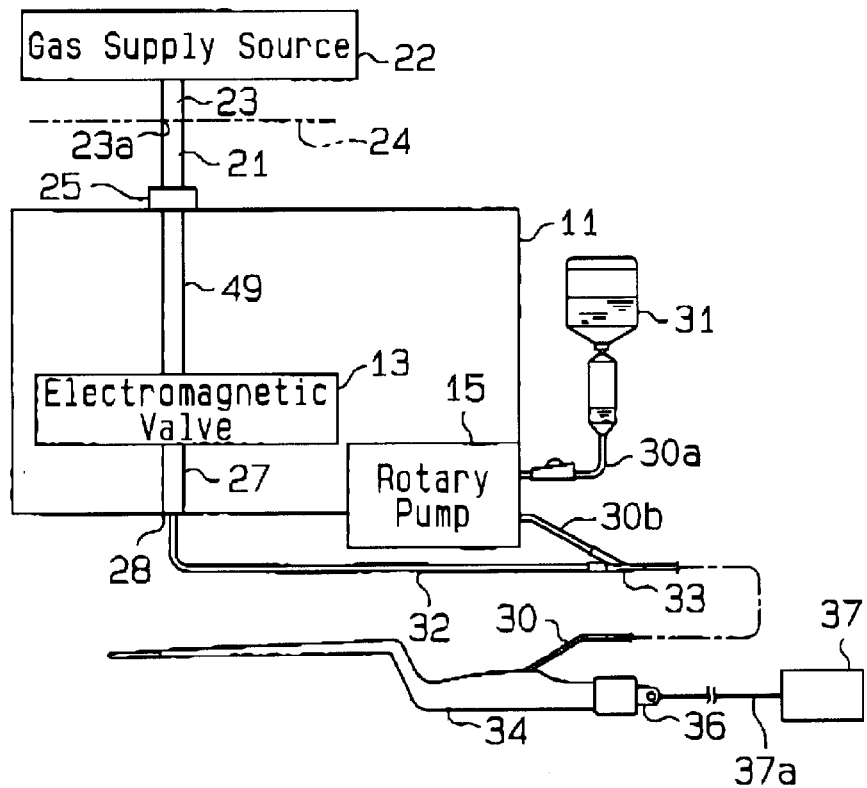
FIG. 6 is a schematic diagram showing electric bipolar tweezers and a perfusate supply apparatus of a third embodiment according to the present invention.

A third embodiment of the present invention will now be described with reference to FIGS. 6 and 7. The description focuses on a difference between the third embodiment and the first embodiment, which is illustrated in FIGS. 1 to 3. As shown in FIG. 6, the third embodiment does not include the air pump 12 or the electromagnetic switch valve 14 or the filter 29, which are illustrated in FIG. 1. The inlet port of the electromagnetic valve 13 is connected to the connector 25 through a connecting pipe 49.

Figure 7:
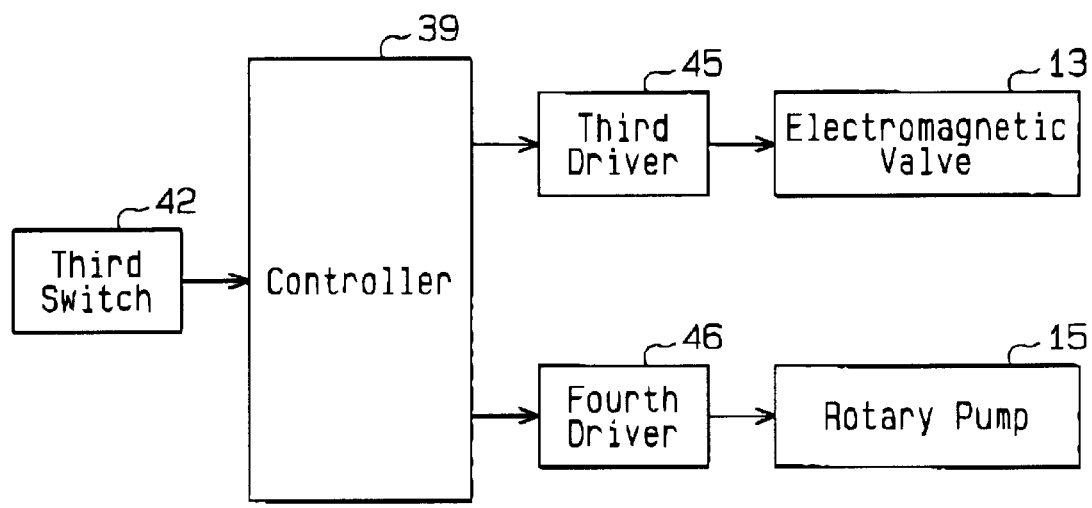
FIG. 7 is a block diagram showing a circuit formed by the perfusate supply apparatus of FIG. 6.

As shown in FIG. 7, only the third switch 42 is connected to the input of the controller 39. Like the first embodiment illustrated in FIGS. 1 to 3, the third switch 42 is selectively turned on and off to activate or de-activate the electromagnetic valve 13 and the rotary pump 15 at the same time.

The operation of the perfusate supply apparatus of the third embodiment will hereafter be described.

First, the manually operated valve (not shown) in the second inlet pipe 21 is opened. In this state, the gas supply source 22 sends carbon dioxide gas to the connecting pipe 49. Subsequently, the third switch 42 is turned on to open the electromagnetic valve 13 while activating the rotary pump 15. Accordingly, like the first embodiment, saline mist is blown from the outlet 38 of the perfusate tube 30.

The third embodiment is configured relatively simple as compared to the first embodiment, which is illustrated in FIGS. 1 to 3. The control box 11 is thus relatively small, and the perfusate supply apparatus is manufactured with low cost.

The present invention may be embodied with the following modifications.

Figure 8:
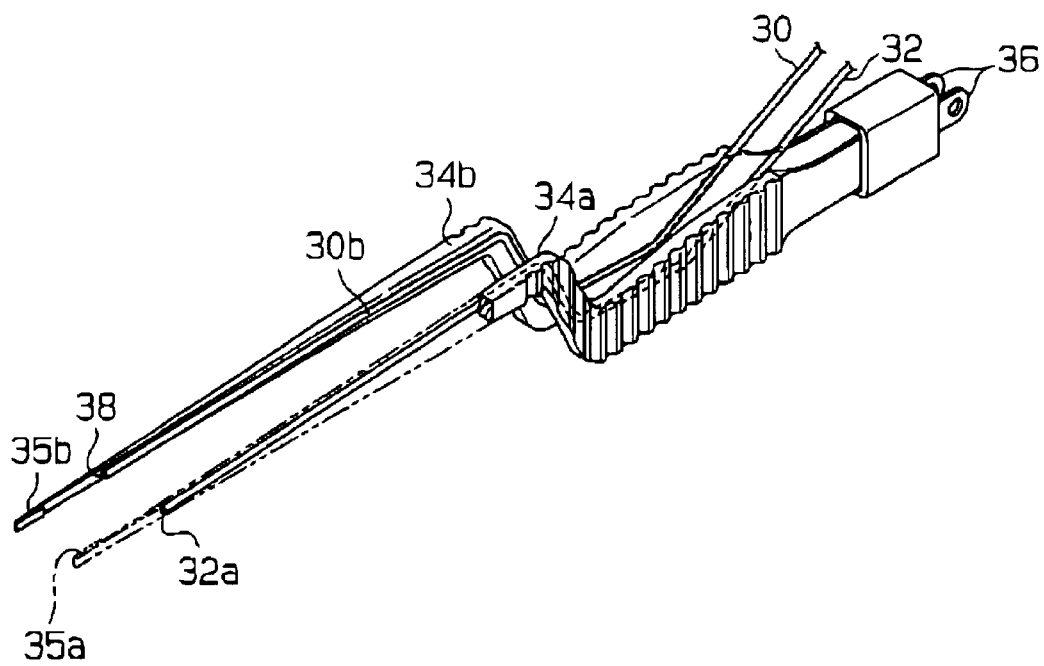
FIG. 8 is a perspective view showing tweezers that include a gas line of a fourth embodiment according to the present invention.

In the embodiments illustrated in FIGS. 1 to 7, the gas line 32 may extend to the tweezers 34 independently from the perfusate tube 30 without being connected to the same. For example, as shown in FIG. 8, the gas line 32 may extend along the elongated portion 34a, while the perfusate tube 30 extends along the elongated portion 34b. The gas line 32 has a gas outlet 32a that opens near the electrode 35a of the elongated portion 34a. The gas outlet 32a is spaced from the electrode 35a toward the proximal end of the elongated portion 34a and faces the electrode 35a.

More specifically, saline is supplied to the vicinity of the electrodes 35a, 35b from the outlet 38 of the perfusate tube 30. Gas is blown from the gas outlet 32a of the gas line 32 toward the electrodes 35a, 35b to prevent saline from being retained between the electrodes 35a, 35b. This structure includes the same operations and advantages as the embodiments illustrated in FIGS. 1 to 7. Alternatively, the gas line 32 may extend adjacent to the perfusate tube 30 along the elongate portion 34b.

In the embodiments illustrated in FIGS. 1 to 5, the air pump 12 may be provided in the exterior of the control box 11.

In the embodiments illustrated in FIGS. 1 to 5, the filter 29 may be detachably attached to the inlet 17.

In the embodiment illustrated in FIGS. 1 to 3 and the embodiment in FIGS. 6 and 7, the gas supply source 22 may supply nitrogen gas, which is also incombustible, instead of carbon dioxide gas.

Liquid other than saline may be used as perfusate.

In the embodiment illustrated in FIGS. 1 to 3 and the embodiment in FIGS. 6 and 7, the electromagnetic valve 13 does not necessarily have to be opened at the same time as the rotary pump 12 is activated. Further, in the embodiment illustrated in FIGS. 4 and 5, the air pump 12 and the rotary pump 15 do not necessarily have to be activated at the same time. In these cases, the timing at which saline starts to flow into the perfusate tube 30 does not correspond to the timing at which gas starts to flow into the perfusate tube 30. Saline or gas is thus blown alone from the outlet 38 before forming a mixture with the other.

The electromagnetic switch valve 14 may be a two-position type. In this case, the switch valve 14 is switched between a first connecting position, which connects the first connecting pipe 18 to the third connecting pipe 26, and a second connecting position, which connects the second connecting pipe 19 to the third connecting pipe 26.

Therefore, the present examples and embodiments are to be considered as illustrative and not restrictive and the invention is not to be limited to the details given herein, but may be modified within the scope and equivalence of the appended claims.

What is claimed is:

1. A perfusate supply apparatus for electric bipolar tweezers, wherein the tweezers include a pair of elongated portions that extend from a base of the tweezers in a forked manner, an electrode is located on a distal end of each elongated portion, and the apparatus comprises:
    a perfusate tube, wherein a perfusate flows in the perfusate tube, and the perfusate tube is attached to the tweezers and has an outlet that opens near one electrode;
    a perfusate pump, which sends the perfusate to the perfusate tube; and
    a gas line, wherein a gas flows in the gas line, and the gas line is connected to an intermediate portion of the perfusate tube for mixing the gas with the perfusate such that a perfusate mist is blown from the outlet of the perfusate tube; and
    an air pump, which sends ambient air to the gas line.

2. The apparatus as set forth in claim 1 further comprising a filter, which infiltrates the ambient air that is sent to the gas line.

3. The apparatus as set forth in claim 1 further comprising an operation switch, which is operated to activate the perfusate pump and the air pump at the same time.

4. The apparatus as set forth in claim 1 further comprising a valve, which is connected to an exterior gas supply source, wherein the valve selectively permits or blocks a gas flow from the gas supply source to the gas line.

5. The apparatus as set forth in claim 4 further comprising an operation switch, which is operated to activate the perfusate pump and open the valve at the same time.

6. The apparatus as set forth in claim 1 further comprising a switch valve, which is switched to send a gas selected from various gases to the gas line.

7. The apparatus as set forth in claim 1, wherein the gas is incombustible.

8. The apparatus as set forth in claim 1, wherein the perfusate tube extends along one elongated portion, and the outlet is spaced from the electrode toward a proximal end of the elongated portion and faces the electrode.

9. A perfusate supply apparatus for electric bipolar tweezers, wherein the tweezers include a pair of elongated portions that extend from a base of the tweezers in a forked manner, an electrode is located on a distal end of each elongated portion, and the apparatus comprises:

- a perfusate tube, wherein a perfusate flows in the perfusate tube, and the perfusate tube is attached to the tweezers and has a prefusate outlet that opens near one electrode;
- a perfusate pump, which sends the perfusate to the perfusate tube to be discharged from the prefusate outlet;
- a gas line, wherein a gas flows in the gas line, the gas line is attached to the tweezers and has a gas outlet that opens toward the electrodes, and the gas discharged from the gas outlet blows away the perfusate between the electrodes; and
- an air pump, which sends ambient air to the gas line.

10. The apparatus as set forth in claim 9 further comprising a filter, which infiltrates the ambient air that is sent to the gas line.

11. The apparatus as set forth in claim 9 further comprising an operation switch, which is operated to activate the perfusate pump and the air pump at the same time.

12. The apparatus as set forth in claim 9 further comprising a valve, which is connected to an exterior gas supply source, wherein the valve selectively permits or blocks a gas flow from the gas supply source to the gas line.

13. The apparatus as set forth in claim 12 further comprising an operation switch, which is operated to activate the perfusate pump and open the valve at the same time.

14. The apparatus as set forth in claim 9 further comprising a switch valve, which is switched to send a gas selected from various gases to the gas line.

15. The apparatus as set forth in claim 9, wherein the gas is incombustible.

16. The apparatus as set forth in claim 9, wherein the gas line is connected to an intermediate portion of the perfusate tube such that part of the perfusate tube functions as the gas line, the prefusate outlet also functions as the gas outlet, and the gas is mixed with the perfusate such that a perfusate mist is blown from the prefusate outlet.

17. A perfusate supply apparatus for electric bipolar tweezers, wherein the tweezers include a pair of elongated portions that extend from a base of the tweezers in a forked manner, an electrode is located on a distal end of each elongated portion, and the apparatus comprises:

- a perfusate tube, wherein a perfusate flows in the perfusate tube, and the perfusate tube is attached to the tweezers and has an outlet that opens near one electrode;
- a perfusate pump, which sends the perfusate to the perfusate tube;
- a gas line, wherein a gas flows in the gas line, and the gas line is connected to an intermediate portion of the perfusate tube for mixing the gas with the perfusate such that a perfusate mist is blown from the outlet of the perfusate tube; and
- a switch valve, which is switched to send a gas selected from various gases to the gas line.

* * * * *

UNITED STATES PATENT AND TRADEMARK OFFICE
CERTIFICATE OF CORRECTION

PATENT NO. : 6,592,583 B2
DATED : July 15, 2003
INVENTOR(S) : Shinichi Hirano et al.

It is certified that error appears in the above-identified patent and that said Letters Patent is hereby corrected as shown below:

<u>Title page,</u>
Item [73], Assignee, replace "Shinichi Hirano, Aichi" with -- Kabushiki Kaisha Tokai Rika DenkiSeisakusho --

Signed and Sealed this

Thirteenth Day of April, 2004

JON W. DUDAS
*Acting Director of the United States Patent and Trademark Office*